(12) United States Patent
Sasada

(10) Patent No.: US 7,912,316 B2
(45) Date of Patent: Mar. 22, 2011

(54) METHOD, APPARATUS AND PROGRAM FOR NOISE SUPPRESSION

(75) Inventor: Ryoji Sasada, Kaisei-machi (JP)

(73) Assignee: Fujifilm Corporation, Tokyo (JP)

( * ) Notice: Subject to any disclaimer, the term of this patent is extended or adjusted under 35 U.S.C. 154(b) by 1455 days.

(21) Appl. No.: 10/755,476

(22) Filed: Jan. 13, 2004

(65) Prior Publication Data

US 2004/0258325 A1 Dec. 23, 2004

(30) Foreign Application Priority Data

Jan. 14, 2003 (JP) .................................. 2003-005715
Dec. 2, 2003 (JP) .................................. 2003-402350

(51) Int. Cl.
*G06K 9/00* (2006.01)
(52) U.S. Cl. ........................ 382/275; 348/607; 358/3.26
(58) Field of Classification Search .................. 382/275, 382/298, 100, 128, 130, 131, 132, 162, 167, 382/254, 255, 260–266, 274; 128/922; 378/4–27; 348/606–624; 358/1.9–3.31
See application file for complete search history.

(56) References Cited

U.S. PATENT DOCUMENTS 5,461,655 A * 10/1995 Vuylsteke et al. .............. 378/62
7,386,158 B2 6/2008 Yamada
2002/0071600 A1* 6/2002 Yamada ........................ 382/132

FOREIGN PATENT DOCUMENTS

JP 10-105701 4/1998
JP 2002-125153 A 4/2002

OTHER PUBLICATIONS

Rafael C. Gonzalez, "Digital Image Processing", 2002, Prentice Hall, 2, 230-231.*
Rafael C. Gonzalez, "Digital Image Processing", 2002, Prentice Hall, pp. 132, 230, 231, 396, 399.*
Baxes, "Digital Image Processing", Sep. 1, 1994, Wiley, 1 ed, p. 441.*

* cited by examiner

*Primary Examiner* — Anand Bhatnagar
(74) *Attorney, Agent, or Firm* — Sughrue Mion, PLLC

(57) ABSTRACT

A band-limited image signal generating unit decomposes an input image signal into a plurality of band-limited image signals, each representing an image having different frequencies. An index value obtaining unit obtains an index value indicating a level of noise suppression based on data representing spatial frequencies as well as an evaluation value representing local contrast at a pixel of interest in band-limited images and data representing an X-ray dose. A noise suppression processing unit performs noise suppression processing on each pixel of each of band-limited images based on the index value. A processed image generating unit obtains a processed image, in which noise has been suppressed, by adding signals obtained by subtracting processed band-limited image signals, of which noise has been suppressed, from the band-limited image signals together, extracting a noise image signal, and subtracting the noise image signal from the input image signal.

16 Claims, 9 Drawing Sheets

(a) IMAGE SIGNAL
(b) VECTOR DATA (FULL-ANGLE) ARROW ON RIGHT SHOWS RELIABILITY OF LINE
(c) VECTOR DATA (DOUBLE-ANGLE) ARROW ON RIGHT SHOWS RELIABILITY OF LINE

BOLD BLACK LINES SHOW DIRECTIONS OF LINES

DEFINITION OF DOUBLE-ANGLE

FILTER FOR $q_0$   FILTER FOR $q_1$   FILTER FOR $q_2$   FILTER FOR $q_3$

METHOD, APPARATUS AND PROGRAM FOR NOISE SUPPRESSION

BACKGROUND OF THE INVENTION

1. Field of the Invention

The present invention relates to a noise suppression processing method and a noise suppression processing apparatus for performing noise suppression processing on an input image signal representing a radiographic image to suppress noise components included in the radiographic image and a program for causing a computer to execute the noise suppression processing.

2. Description of the Related Art

Generally, when radiographic images obtained by computed radiography devices (hereinafter called CR devices) or the like are used in diagnoses, the obtained radiographic images are processed into appropriate images for diagnoses with a desired method such as frequency emphasis processing and gradation processing. The processed images are displayed on CRT monitors as soft copies or output to films as hard copies.

At this time, there is a problem that quantum noise in radiation is noticeable in low density areas of the radiographic images, where radiation doses were small. Therefore, various noise suppression processing methods have been proposed to suppress noise components included in image signals representing radiographic images.

U.S. Patent Laid-Open No. 20020071600 proposes a method for obtaining an original image, in which noise components have been suppressed, by performing multi-resolution decomposition to decompose an original image into a sequence of detail images (band-limited image signals at resolution levels 1-M), obtaining an index value indicating a level of noise suppression based on data representing a radiation dose, suppressing noise components in each of the detail images based on the index value and reconstructing an image from each of the detail images, of which noise components have been suppressed, for example.

Further, U.S. Patent Laid-Open No. 20020071600 proposes a method for suppressing noise components of each of detail images by calculating noise characteristics based on data representing a radiation dose and switching characteristics of a smoothing filter, applied to each of the detail images based on the noise characteristics.

It is known that the amount of noise components included in a radiographic image depends on spatial frequencies of the radiographic image as well as a radiation dose during radiographic photography when the radiographic image is obtained (If the spatial frequencies are higher, the noise amount is larger).

However, when the level of noise suppression is determined, the spatial frequencies are not considered in the methods disclosed in U.S. patent Laid-Open No. 20020071600 as described above. Therefore, suppression of the noise components in the radiographic images by these methods is insufficient.

SUMMARY OF THE INVENTION

In view of the foregoing circumstances, it is an object of the present invention to provide a noise suppression processing method and a noise suppression processing apparatus, which can suppress the noise components in the radiographic images more effectively, and a program for causing a computer to execute the noise suppression processing.

The noise suppression processing method according to the present invention is a noise suppression processing method for performing noise suppression processing on an input image signal representing an input radiographic image to suppress noise components included in the radiographic image. The method includes the steps of: generating a plurality of band limited image signals, each representing an image having different frequency bands, based on the radiation image;

obtaining an index value indicating the level of noise suppression to be administered to suppress the noise components, based on data representing the radiation dose during obtainment of the radiation image, and data representing spatial frequencies of the radiation image; and administering the noise suppression process on each of the plurality of band limited image signals based on the index value.

The noise suppression processing apparatus according to the present invention is a noise suppression processing apparatus for performing noise suppression processing on an input image signal representing an input radiographic image to suppress noise components included in the radiographic image. The apparatus includes: a band limited image signal generating means for generating a plurality of band limited image signals, each representing an image having different frequency bands, based on the radiation image;

an index value obtaining means for obtaining an index value indicating the level of noise suppression to be administered to suppress the noise components, based on data representing the radiation dose during obtainment of the radiation image, and data representing spatial frequencies of the radiation image; and a noise suppression processing means for administering the noise suppression process on each of the plurality of band limited image signals based on the index value.

The "data representing a radiation dose during obtainment of the radiographic image" may be data (corresponding to the dose), which can indirectly represent the radiation dose, such as a photography menu, a patient's age, a photography condition (irradiating condition of a photography device), a standardization condition (refer to Japanese Unexamined Patent Publication No. 2(1990)-108175, etc.) and a signal value (density value) of an image as well as data that can directly represent the radiation dose during obtainment of the radiographic image, such as data from a photo timer.

The "data representing spatial frequencies of the radiographic image" may be a value that varies according to the spatial frequencies, such as an image number corresponding to a resolution level of a band-limited image as well as data that directly represent the spatial frequencies.

It is desirable that the band-limited image signal generating means generates a plurality of band-limited image signals by performing multi-resolution decomposition on an input image signal. At this time, signals representing noise components in each of band-limited images are obtained by subtracting band-limited image signals after processing from band-limited image signal before noise suppression processing. The signals representing the noise components are added together and a noise image signal representing the noise components of the input image signal is obtained. A processed image, in which noise has been suppressed, is obtained by subtracting the noise image signal from the input image signal. Alternatively, the image may be reconstructed by performing inverse multi-resolution development directly on the band-limited image signals, on which noise suppression processing has been performed. Laplacian pyramid decomposition, wavelets transformation or the like should be used as the multi-resolution decomposition.

In the noise suppression processing apparatus according to the present invention, the index value obtaining means may obtain the index value by calculating noise characteristics of the radiographic image, based on data representing dose and the data representing spatial frequencies and deriving the index value based on the noise characteristics.

An example of the "noise characteristics" is a threshold value, which is used as standards for judging whether a signal of the pixel is noise, at the pixel of interest. The threshold value may be either theoretically calculated or obtained by experiments or experience.

Further, the index value obtaining means may obtain the index value for each pixel of band-limited images represented by the band-limited image signals. The noise suppression processing means may perform the noise suppression processing on each of the pixels, based on the index value for each of the pixels.

The index value obtaining means may obtain the index value for each pixel of band-limited images represented by the band-limited image signals, by calculating the noise characteristics thereof. The noise suppression processing means may perform the noise suppression processing on each of the pixels, based on the index value for each of the pixels.

Further, the index value obtaining means may obtain the index value by obtaining an evaluation value based on values of band-limited signals in the vicinity of the pixel and deriving the index value based on the evaluation value and the noise characteristics.

It is preferable that a value representing a local contrast in density at the pixel of interest, such as pixel energy at the pixel of interest is used as the "evaluation value". The pixel energy is obtained as an average of magnitudes (values) of each of vector components when a density gradient in the vicinity of the pixel of interest is represented by vector components in four directions at intervals of 45 degrees. If the signal is a point signal with a high local contrast, the pixel energy is high. On the contrary, if the signal is a point signal with a low contrast, the pixel energy is low.

A program according to the present invention is a program for causing a computer to execute noise suppression processing on an input image signal representing an input radiographic image to suppress noise components included in the radiographic image. The noise suppression processing includes: a procedure for generating a plurality of band limited image signals, each representing an image having different frequency bands, based on the radiation image;

a procedure for obtaining an index value indicating the level of noise suppression to be administered to suppress the noise components, based on data representing the radiation dose during obtainment of the radiation image, and data representing spatial frequencies of the radiation image; and a procedure for administering the noise suppression process on each of the plurality of band limited image signals based on the index value.

In the program according to the present invention, the procedure of obtaining the index value may be the procedure of obtaining the index value by calculating noise characteristics of the radiographic image, based on the data representing the dose and the data representing the spatial frequencies and deriving the index value based on the noise characteristics.

Further, the procedure of obtaining the index value may be the procedure of obtaining the index value for each pixel of the band-limited images represented by the band-limited image signals. The procedure of performing the noise suppression processing may be the procedure of performing the noise suppression processing on each of the pixels, based on the index value for each of the pixels.

Further, the procedure of obtaining the index value may be the procedure of obtaining the index value for each pixel of band-limited images represented by the band-limited image signals, by calculating the noise characteristics thereof. The procedure of performing the noise suppression processing may be the procedure of performing the noise suppression processing on each of the pixels, based on the index value for each of the pixels.

Further, the procedure of obtaining the index value may be the procedure of obtaining the index value by obtaining an evaluation value based on values of band-limited signals in the vicinity of the pixel and deriving the index value based on the evaluation value and the noise characteristics.

In the noise suppression processing method, apparatus and program according to the present invention, the index value indicating the level of noise suppression to be administered to suppress the noise components is obtained based on the data representing the spatial frequencies of the radiographic image as well as the data representing the radiation dose during obtainment of the radiographic image as data correlated with a noise amount included in the radiographic image. The noise suppression processing is performed on each of the plurality of band-limited image signals based on the obtained index value. Therefore, a single image signal can be reconstructed based on each of the band-limited image signals, on which noise suppression processing has been performed. Alternatively, an image, in which noise has been more effectively suppressed, may be obtained by extracting differences between the band-limited image signals and the band-limited image signals, of which noise has been suppressed as noise signals, synthesizing the extracted noise signals and subtracting the synthesized noise signals from the input image signal.

Further, at the time of noise suppression processing, the index values may be obtained for each of the plurality of band-limited image signals and the noise suppression processing may be performed on each of the band-limited image signals. Alternatively, the index values may be obtained for each pixel of the band-limited images represented by the band-limited image signals and the noise suppression processing may be performed on each of the pixels. Accordingly, optimum index values for each area in the image can be used in each of the areas of the image. Consequently, finer noise suppression processing can be performed compared with the case of obtaining the index value based on an average of the entire image and performing the noise suppression processing based on the index value, for example.

DESCRIPTION OF THE PREFERRED EMBODIMENTS

Embodiments of the noise suppression processing apparatus according to the present invention will be described below.

Figure 1:
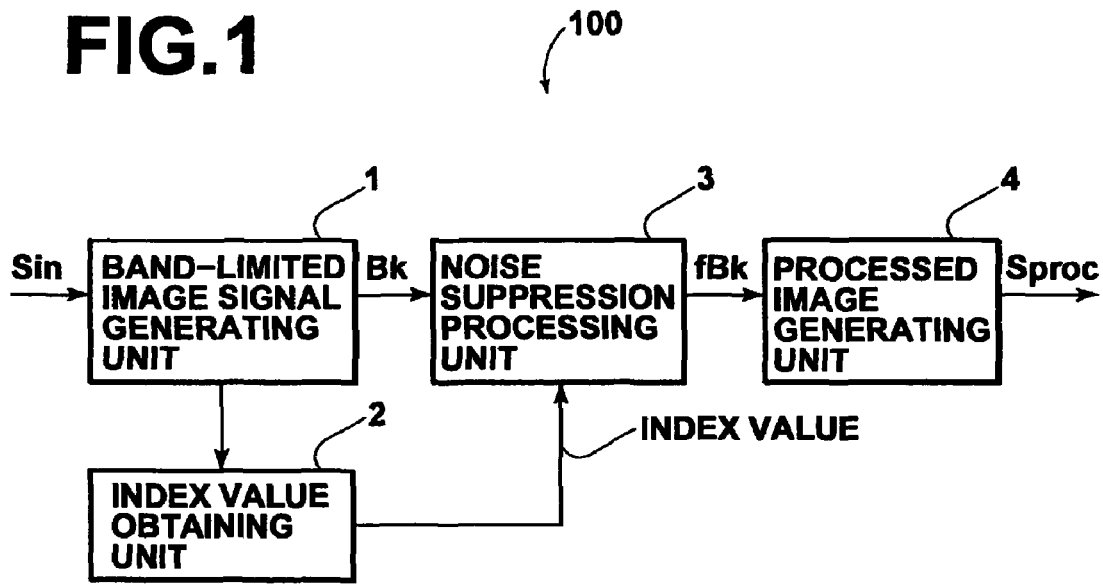
FIG. 1 shows a schematic block diagram illustrating a configuration of a noise suppression processing apparatus in an embodiment of the present invention.

FIG. 1 shows a schematic block diagram showing a configuration of the noise suppression processing apparatus according to an embodiment of the present invention.

A noise suppression processing apparatus 100 includes: a band-limited image signal generating unit 1 for generating a plurality of band-limited image signals, each representing images having different frequency bands, based on an input image signal Sin representing a radiographic image having a predetermined resolution, obtained by using a reading device or the like; an index value obtaining unit 2 for obtaining an index value indicating a level of noise suppression to be administered to suppress the noise components, based on data representing a radiation dose during obtainment of the radiographic image and data representing spatial frequencies of the radiographic image; a noise suppression processing unit 3 for performing the noise suppression processing on each of the plurality of band-limited image signals based on the obtained index value; and a processed image generating unit 4 for generating a processed image signal Sproc representing a radiographic image, in which noise has been suppressed, based on the plurality of band-limited images, on each of which noise suppression processing has been performed, as illustrated in FIG. 1.

The index value obtaining unit 2 obtains the index value based on evaluation values and noise characteristics by obtaining an evaluation value based on values of band-limited signals in the vicinity of each pixel in each of the band-limited images and also calculating the noise characteristics of the radiographic image based on the data representing the radiation dose and the data representing the spatial frequencies.

The noise suppression processing unit 3 performs the noise suppression processing for each pixel of band-limited image signals Bk, based on the index value for each of the pixels, obtained by the index value obtaining unit 2.

Further, a subject of the noise suppression processing in the present embodiment is a digital image signal read by scanning a radiographic image of a human body recorded on a stimulable phosphor sheet with laser beams in a radiographic image data recording/reproducing system using stimulable phosphor sheets as disclosed in Japanese Unexamined Patent Publication No. 55(1980)-12492 and Japanese Unexamined Patent Publication No. 56(1981)-11395, for example. The radiographic image is read by scanning the sheet two-dimensionally. The stimulable phosphor sheet is moved in a sub-scanning direction (vertical direction) while the stimulable phosphor sheet is scanned with the laser beams in a main scanning direction (horizontal direction).

Next, the operation of the noise suppression processing apparatus 100, which is configured as described above, will be described.

Figure 2:
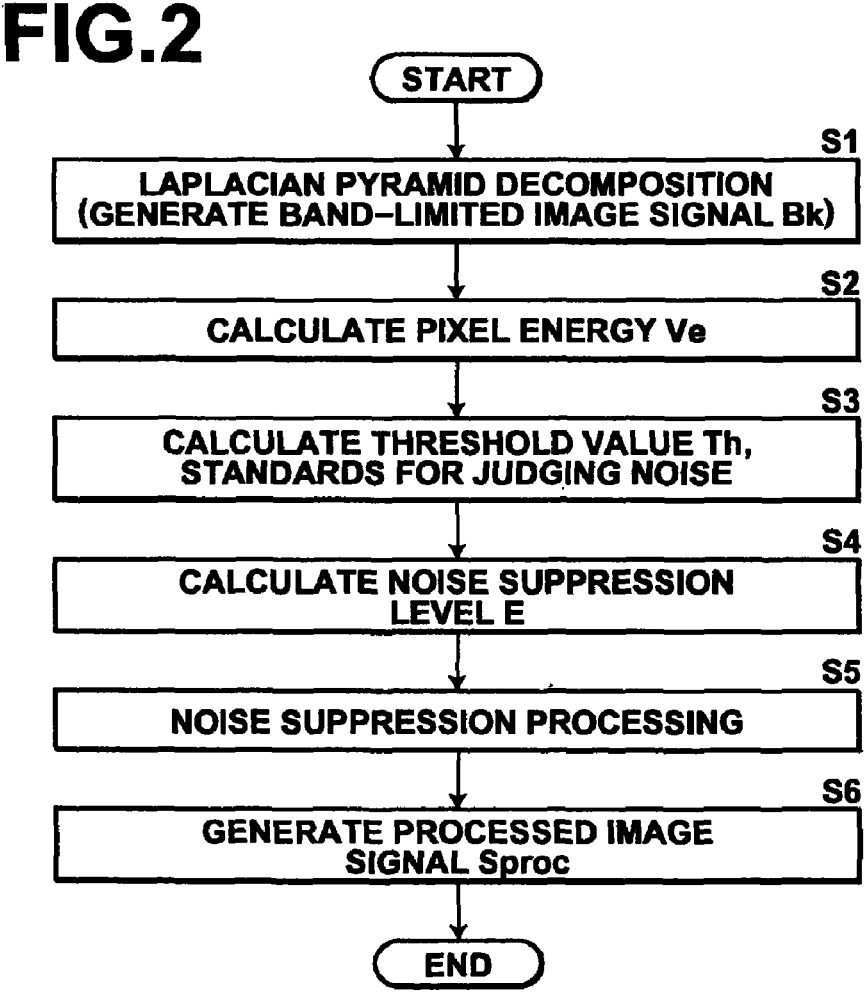
FIG. 2 shows a flow chart showing a processing procedure by the noise suppression processing apparatus according to the present invention.

First, an outline of the processing will be described with reference to the flow chart illustrated in FIG. 2.

Multi-resolution transformation techniques such as Laplacian pyramid decomposition as disclosed in Japanese Unexamined Patent Publication No. 5(1993)-244508 and Japanese Patent No. 3193806 or as proposed by the applicant of the present application in Japanese Unexamined Patent Publication No. 2001-57677, Japanese Unexamined Patent Publication No. 2000-306089, etc. and wavelet transformation as proposed by the applicant of the present application in Japanese Patent No. 3205417 and Japanese Unexamined Patent Publication No. 2001-57677, etc. should be used to generate the band-limited image signals. Further, other known methods such as a method of obtaining the band-limited image signal by using an unsharp masking signal as disclosed in Japanese Unexamined Patent Publication No. 10(1998)-75364 may be used. It is assumed that the Laplacian pyramid technique is used in the description of the following embodiments.

Band-limited image signals are obtained from an input original image by using the Laplacian pyramid decomposition technique, which is an example of the multi-resolution transformation (Step S1). Then, pixel energy Ve at each pixel position of each of the band-limited images, which have been decomposed into multi-resolution spaces and are represented by the band-limited image signals, is calculated as an evaluation value in the present invention (Step S2). The pixel energy Ve is calculated by obtaining vector components in four directions at intervals of 45 degrees at a position of a pixel of interest using Double-Angle representation, which will be described later.

Next, a threshold value Th, which will be used as standards for judging whether the signal is noise having the noise characteristics in the present invention, is obtained based on an index x representing the radiation dose during obtainment of the original image and an index r representing the spatial frequencies of the original image (Step S3).

A noise suppression level E as an index value indicating a level of noise suppression is calculated based on the pixel energy Ve and the threshold value Th, which have been obtained as described above (Step S4). The noise suppression processing is performed by filtering using the noise suppression level E (Step S5). Then, band-limited noise image signals, which are difference signals between the band-limited image signals and the band-limited image signals of which noise has been suppressed, are obtained and the band-limited noise image signals for each of the band-limited signals are added together. The sum of the signals is subtracted from the original image signal and a processed image is obtained (Step S6).

Next, processing in each of the steps will be described in detail.

(Generation of Band-Limited Image Signal Bk)

Figure 3:
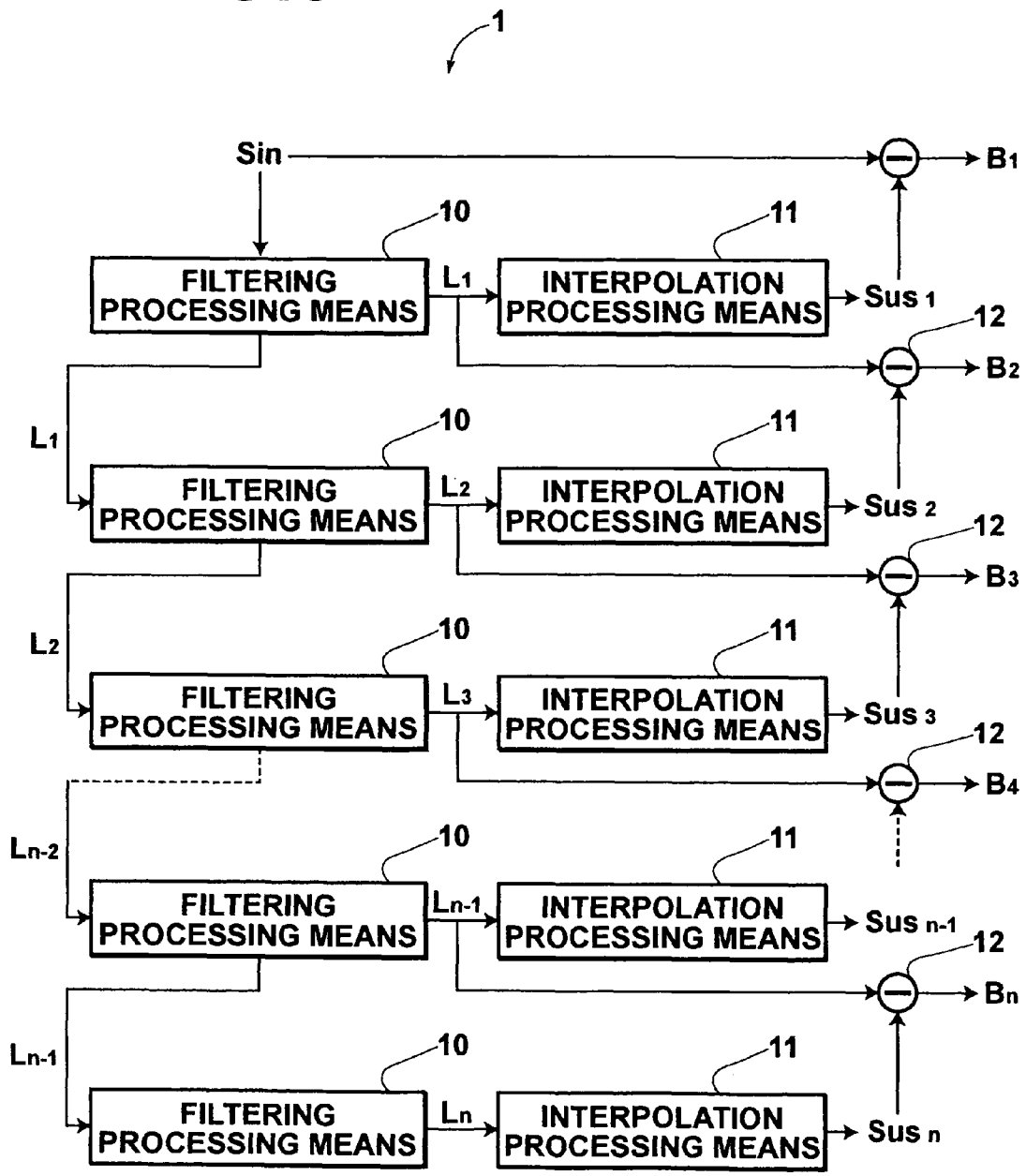
FIG. 3 shows a block diagram schematically showing a band-limited image signal generating unit.
Figure 4:
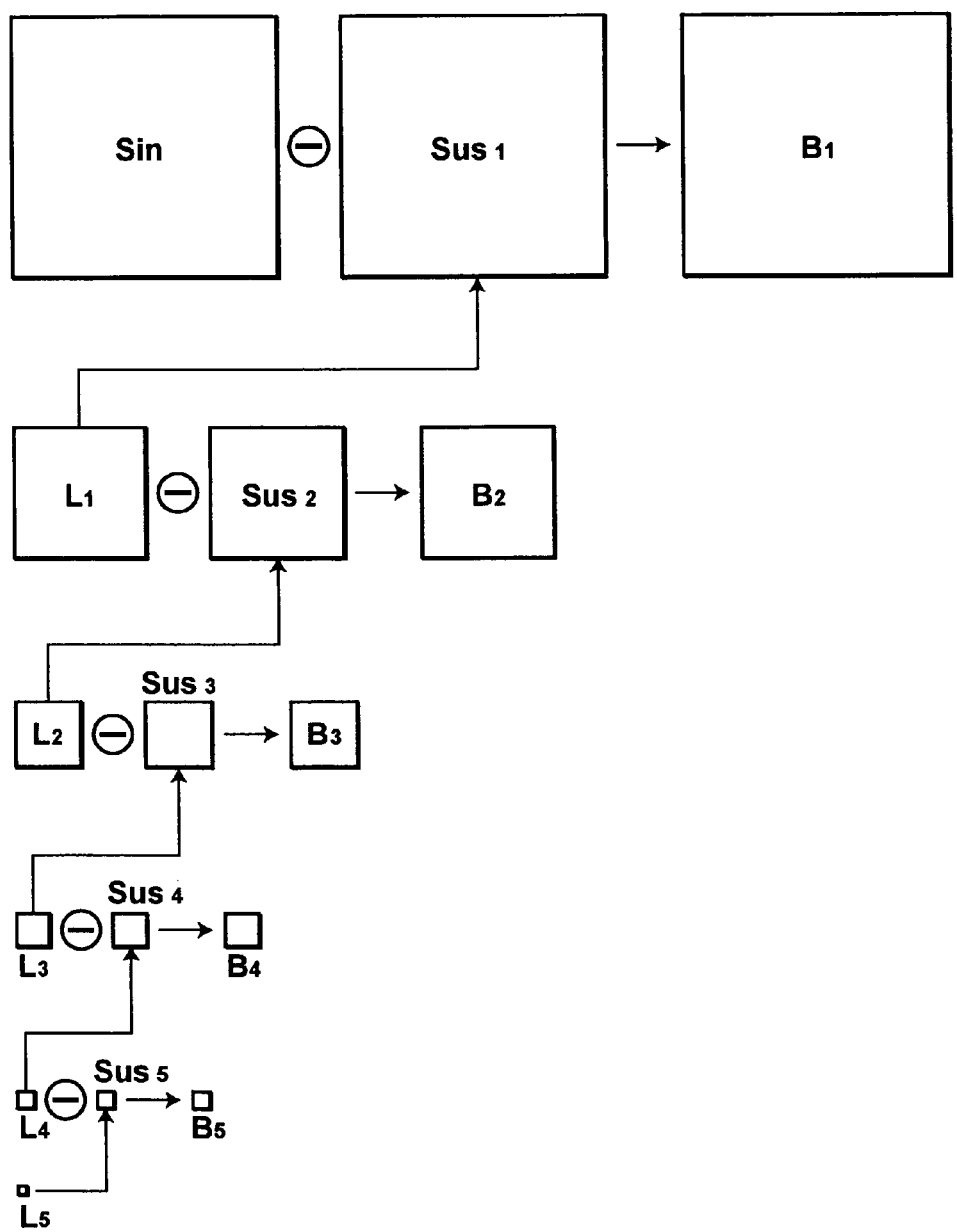
FIG. 4 shows a diagram schematically illustrating processing for generating band-limited image signals.

FIG. 3 shows a schematic block diagram illustrating the band-limited image signal generating unit 1. FIG. 4 schematically illustrates processing for generating the band-limited image signals at five levels.

A filtering processing means 10 generates an image signal L1 (hereinafter called a low resolution image signal), of which resolution is lower than the resolution of the input image signal Sin, by performing filtering processing on the input image signal Sin in each of a main scanning direction and a sub-scanning direction of the original image, as disclosed in Japanese Unexamined Patent Publication No.

5(1993)-244508, for example. Next, a low resolution image signal L2, of which resolution is even lower than that of the low resolution image signal L1, is generated by performing filtering processing on the low resolution image signal L1. The same filtering processing is repeated sequentially and low resolution image signals Lk (k=1 to n) are obtained. Then, an interpolation processing means 11 performs interpolation processing on the low resolution image signals Lk obtained in each step of filtering processing so that numbers of pixels will be doubled in each of the main scanning direction and the sub-scanning direction (quadrupled in total). Consequently, a plurality of unsharp masking image signals Sus1 to Susn (hereinafter represented by Susk (K=1 to n)) at various sharpness levels are obtained. Then, a difference between the low resolution image signal Lk-1 and the unsharp masking image signal Susk that have corresponding numbers of pixels and a difference between the input image signal Sin and the unsharp masking image signal Sus1 that have corresponding numbers of pixels are obtained by a subtractor 12 and the differences are used as the band-limited image signals Bk.

Next, the steps of obtaining the index value (noise suppression level) indicating the level of noise suppression using the band-limited image signals Bk obtained as described above and performing the noise suppression processing based on the obtained index value will be described.

Figure 5:
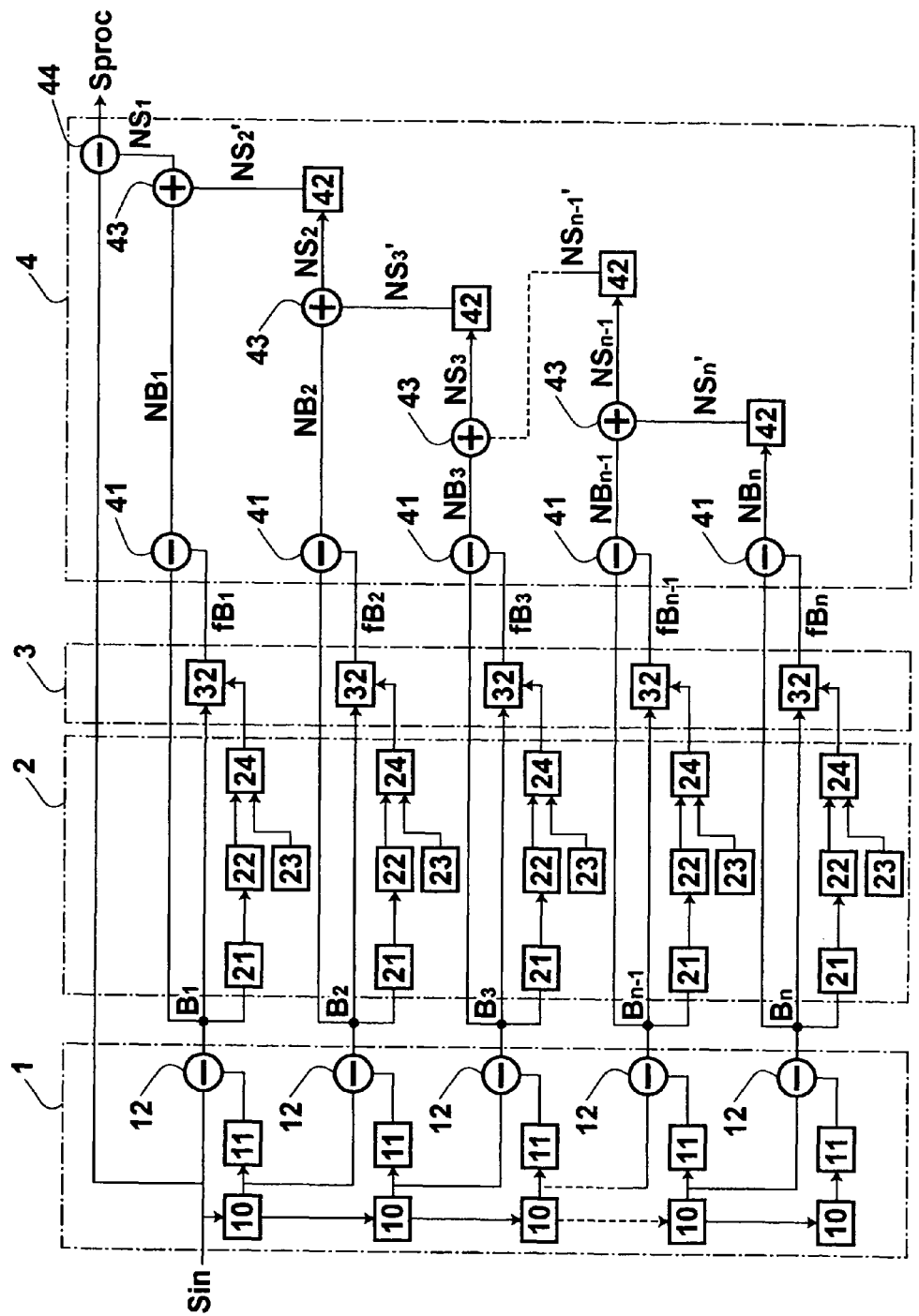
FIG. 5 shows a block diagram showing details of a whole configuration of the noise suppression processing apparatus.

FIG. 5 shows a block diagram illustrating the entire configuration of the apparatus 100 in detail. As illustrated in FIG. 5, the index value obtaining unit 2 includes a pixel vector obtaining means 21 for obtaining a pixel vector at each pixel in each of the band-limited images represented by each of the band-limited image signals Bk; an evaluation value calculating means 22 for obtaining the pixel energy Ve (an example of the evaluation value in the present invention) for each pixel in each of the band-limited images based on a length and/or direction of the pixel vector; a noise characteristics calculating means 23 for calculating the threshold value Th (an example of the noise characteristics in the present invention) for each pixel in each of the band-limited images based on the index x representing the dose and the index r representing the spatial frequencies; and an index value calculating means 24 for calculating the noise suppression level E (an example of an index value indicating a level of noise suppression in the present invention) for each pixel based on the pixel energy Ve and the threshold value Th obtained for each pixel in each of the band-limited images.

The noise suppression processing unit 3 includes a suppression processing means 32 for performing processing to suppress noise components included in the band-limited image signals Bk, based on the index value output from the index value calculating means 24, for each of the band-limited image signals Bk.

A technique of "changing a level of noise suppression according to an index representing noise characteristics and suppressing a signal with higher noise characteristics at a higher suppressing level" is used in the noise suppression processing in the present embodiment. Specifically, the index indicating the noise characteristics is represented by a ratio of the strength of a local contrast to a threshold value, which will be used as standards for judging whether the signal is noise at a certain pixel position. A function that becomes closer to 0 (zero) with a decrease in the ratio and becomes closer to 1 with an increase in the ratio is defined as a noise suppression level and an operation of multiplying a signal at the pixel by the noise suppression level is performed. Through this operation, a strong point signal (pixel) with high contrast, which is judged as an actual image, remains and a weak point signal (pixel) with weak contrast, which is judged as noise, is suppressed or eliminated. In the present embodiment, the local contrast is represented by the pixel energy.

(Calculation of Pixel Energy Ve)

The pixel energy Ve is calculated by obtaining vector components q0 to q3 in four directions (not orientations) at intervals of every 45 degrees at a certain pixel position using Double-Angle representation (hereinafter, called D-A representation). The pixel energy Ve is calculated as an average of each of vector components by using Formula (1):

[Formula 1]

$$Ve = (q_0 + q_1 + q_2 + q_3)/4 \quad (1)$$

Figure 6:
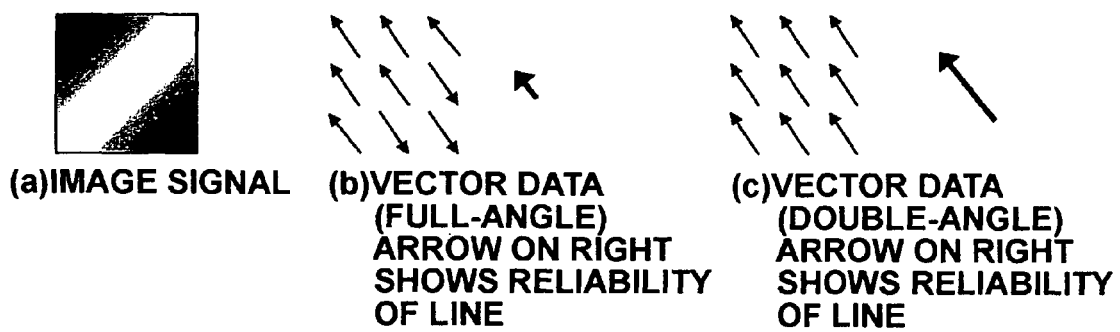
FIG. 6 shows a conceptual diagram for describing Double-Angle representation.

The D-A representation of the vectors is a technique for representing a line signal. The D-A representation has the merit as an algorithm in that reliability (index of line characteristics) of the line signal can be calculated only by obtaining the vicinity average of data represented using the D-A representation. This merit will be described briefly with reference to FIG. 6.

Density vectors of the image signal as illustrated in FIG. 6(a) are calculated. The density vectors are represented using normal vector representation (in this case, Full-Angle representation; hereinafter called F-A representation) as illustrated in FIG. 6(b). The directions of the vectors in the areas divided by a low density area in the middle are opposite. Meanwhile, since the calculated vector angle is doubled in the D-A representation, the density vectors are represented as illustrated in FIG. 6(c).

Reliability C of line signal is calculated based on the vicinity average of the vectors. The reliability C is indicated by big arrows in the right side of (B) and (c). The reliability of (b) is much lower than the reliability of (c). Although not illustrated, it can easily be imagined that the noise (for which vectors in the vicinity point to various directions) also has lowered reliability. Therefore, it is more difficult to separate the noise from the line data in the F-A representation.

Figure 7:
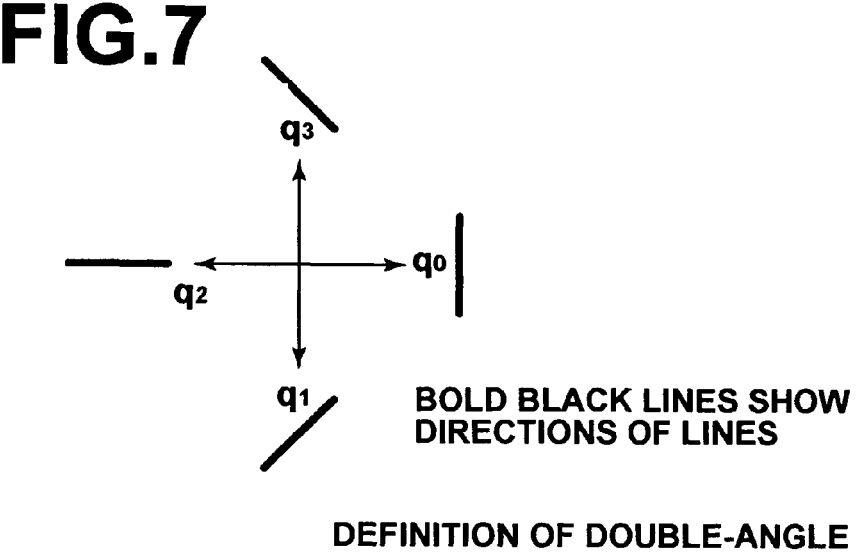
FIG. 7 shows a diagram for describing a definition of Double-Angle representation.

On the contrary, the vectors are defined with respect to the directions of lines using the D-A representation as illustrated in FIG. 7. The components q0 to q3 represent magnitudes of the components in each direction at the pixel of interest. In the case that the magnitudes of components in two orthogonal directions are equal (corresponding to an intersection), an output is weak in the D-A representation. If the magnitudes of two orthogonal components are different, the direction of the larger component becomes a main direction.

Therefore, the vectors can be represented using the D-A representation by calculating the components q0 to q3 in four directions at each pixel.

Here, a method for calculating each of the directional components q0 to q3 will be described specifically.

Figure 8:
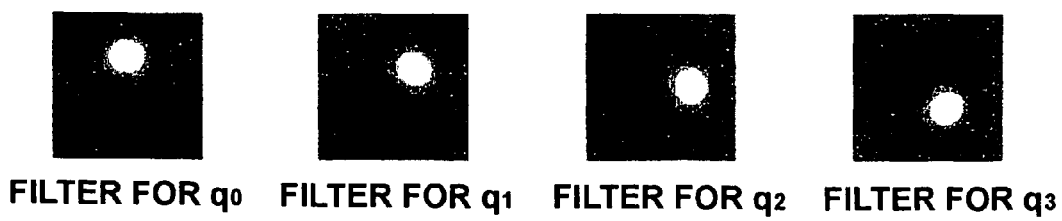
FIG. 8 shows a diagram illustrating examples of four kinds of two-dimensional spatial filters.

The band-limited image signals, which are the subject of the present invention, are Laplacian pyramid signals generated by Laplacian pyramid decomposition. Four components are calculated by convolution with four kinds of two-dimensional spatial filters as illustrated in FIG. 8. Filter coefficients of a 5×5 q0 filter is shown in TABLE 1 as an example of filter coefficients. Since both of the Laplacian signals and the filter coefficients are positive or negative values with respect to zero, absolute values of the convolution products are used as directional components.

TABLE 1

| Filter Coefficient for q0 (in the Case of 5 × 5) | | | | |
|---|---|---|---|---|
| 0.0012 | 0.0211 | 0.0577 | 0.0211 | 0.0012 |
| 0.0053 | 0.1389 | 0.6093 | 0.1389 | 0.0053 |
| 0.0000 | 0.0000 | 0.0000 | −0.0000 | −0.0000 |

TABLE 1-continued

Filter Coefficient for qo (in the Case of 5 × 5)

| −0.0053 | −0.1389 | −0.6093 | −0.1389 | −0.0053 |
| −0.0012 | −0.0211 | −0.0577 | −0.0211 | −0.0012 |

(Calculation of Threshold Value Th)

The threshold value, which will be used as standards for judging whether the signal is noise, depends on the dose and the spatial frequencies. Therefore, the threshold value Th may be represented by a function using the index x representing an X-ray dose and index r representing the spatial frequencies as parameters. In the case that the radiographic image is used as the subject image for processing as in this embodiment, The X-ray dose can be estimated from value S (reading sensitivity) and value L (latitude). The index x defined by equation (2) may be used, for example. Please refer to Japanese Unexamined Patent Publication No. 2(1990)-108175 regarding the value S and the value L, for example.

[Formula 2]

$$\left.\begin{array}{c} X = (1/ValueS) \times 10^{(ValueL \times QL/1024)} \\ QL: \text{Signal Value}, X: \text{Relative X-Ray Dose} \end{array}\right\} \quad (2)$$

Here, QL is a signal value for a pixel. It is assumed that the signal value is represented in 10 bits in Formula (2).

In the case that the original image signal Sin is decomposed into band-limited image signals Bk for each frequency band by Laplacian pyramid decomposition, since each of the band-limited image signals Bk correspond to the images each having different spatial frequencies, numbers k of the band-limited image signals may be used as the indexes r, for example.

Figure 9:
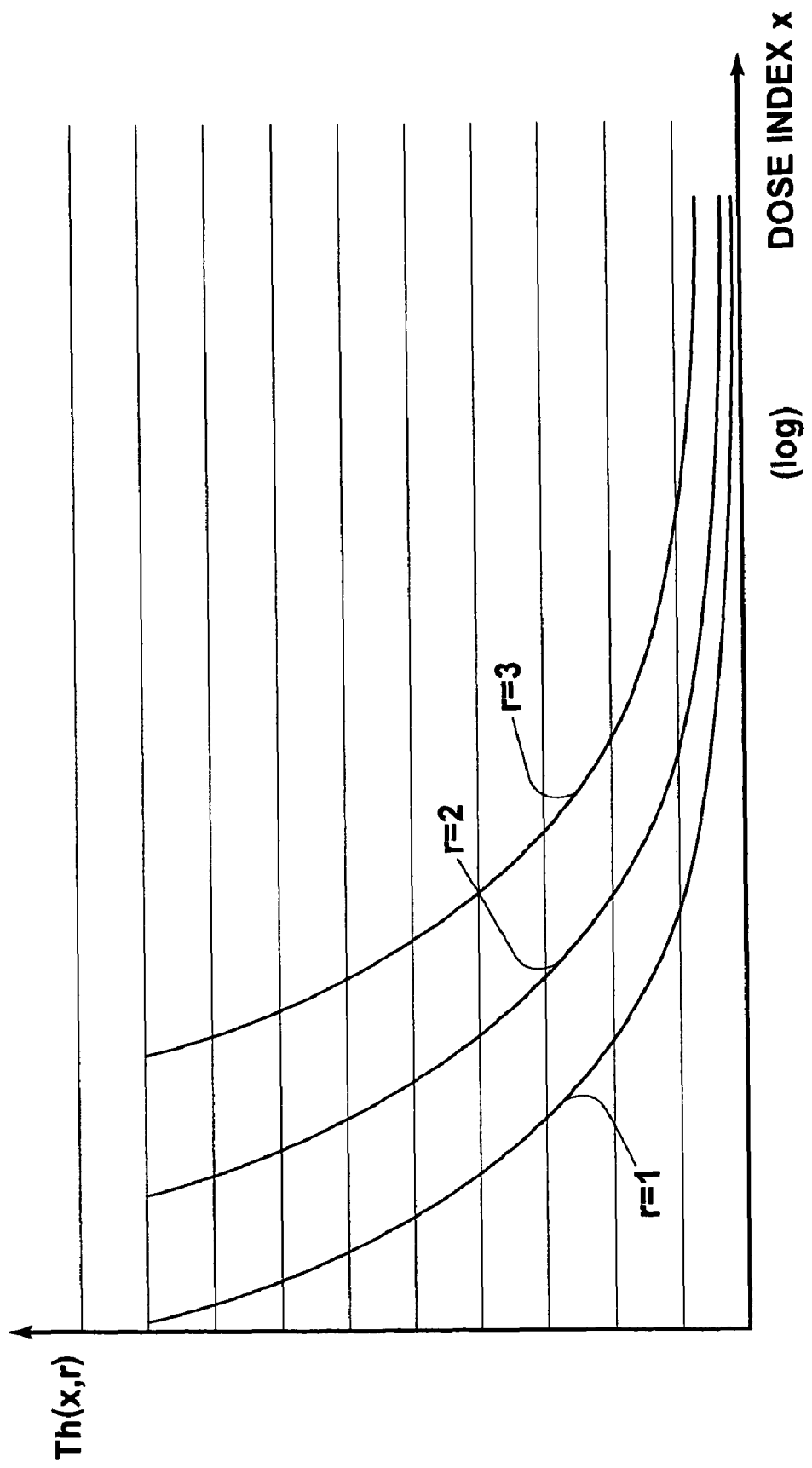
FIG. 9 shows chart illustrating an example of curves of threshold values, which will be used as standards for judging whether there is noise.
Figure 10:
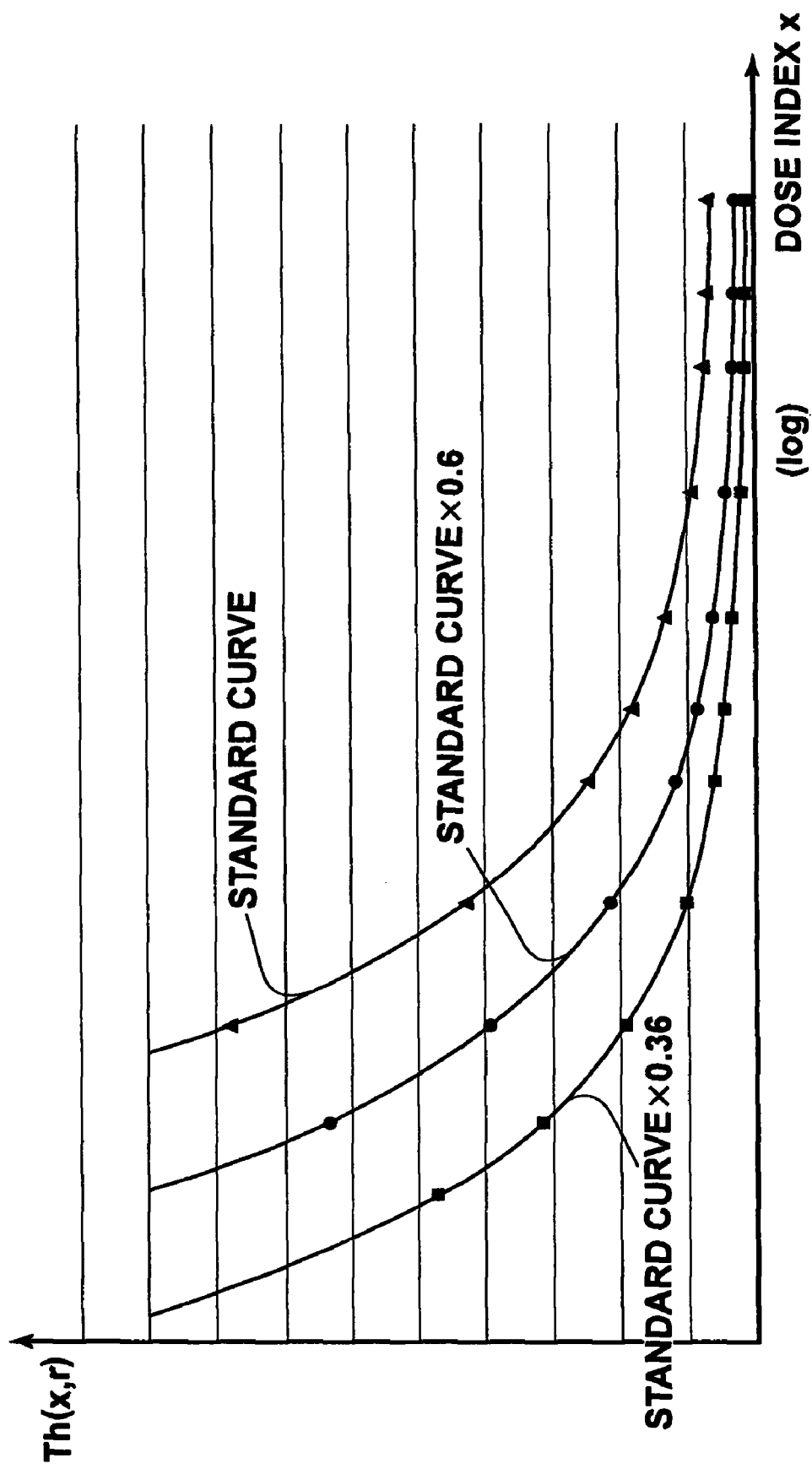
FIG. 10 shows a chart illustrating an example of curves of threshold values provided as intersection point data.

Meanwhile, the noise has the characteristics that the noise amount increases when the X-ray dose is lower and the spatial frequencies are higher. Therefore, the threshold value Th becomes larger when the X-ray dose is lower, i.e., index x is lower. The threshold value Th becomes larger when the spatial frequencies are higher, i.e., the index r is lower. Therefore, curves showing threshold values Th are set as illustrated in FIG. 9 and the threshold values Th for each of the index x and the index r are derived from the curves. The threshold value Th may be represented by a numerical Formula using the index x and the index r as variables. However, in some cases, it is difficult to obtain an ideal curve by a numerical Formula. Therefore, a standard curve ThBase(x) may be provided as intersection point data including some pairs of (x, ThBase(x)) and coefficient ThCo(r) for each index r may be also provided. Then, the threshold value Th may be obtained by multiplying the standard curve by the coefficient as illustrated in Formula (3).

[Formula 3]

$$Th(x,r) = ThBase(x) \times ThCo(r) \quad (3)$$

(Calculation of Noise Suppression Level E)

Figure 11:
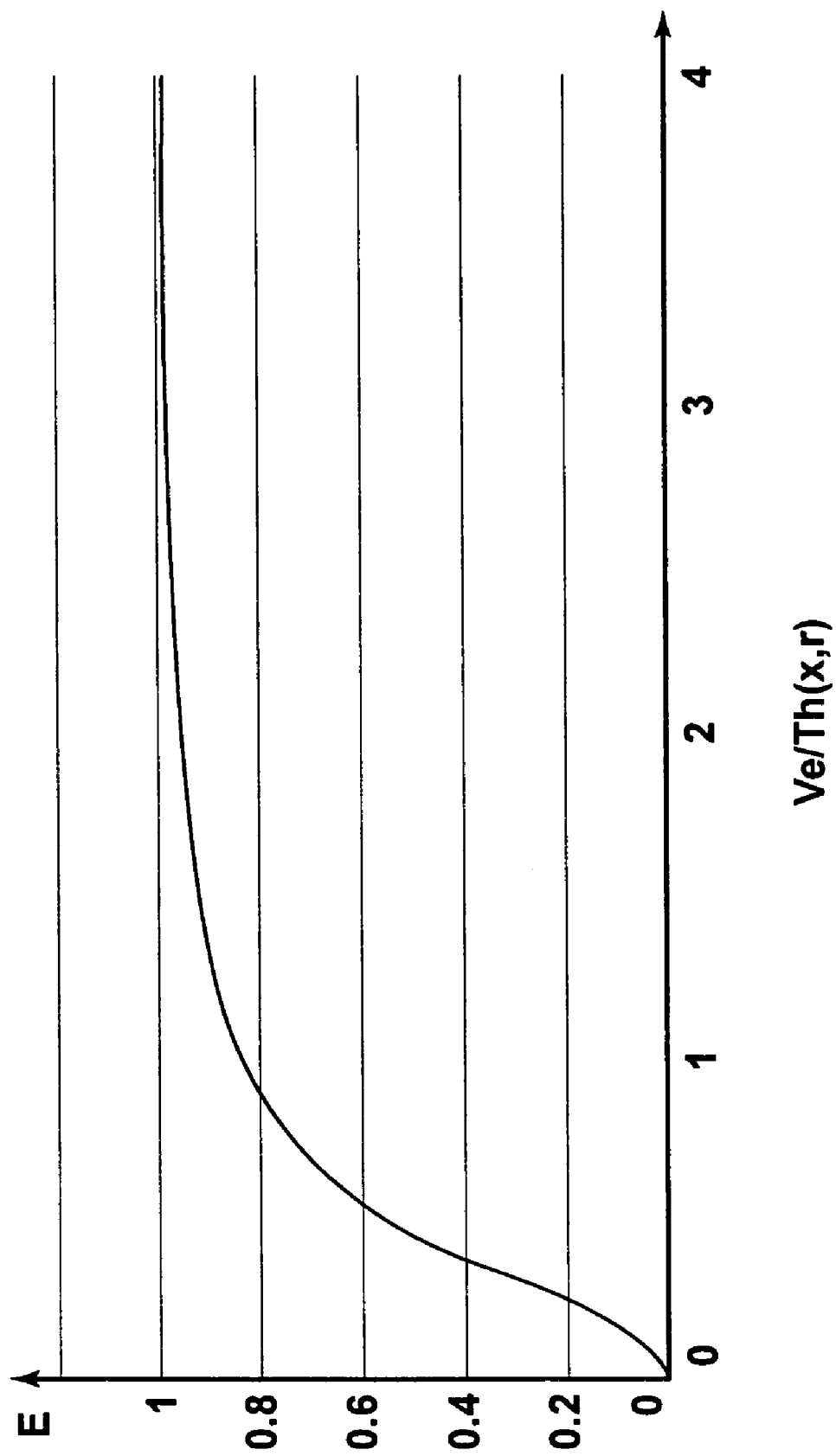
FIG. 11 shows a chart showing an example of curves of noise suppression levels.

As described above, the noise suppression processing in the present embodiment is the processing of "changing a level of noise suppression according to an index representing noise characteristics and suppressing a signal with higher noise characteristics at a higher suppressing level". Therefore, the index representing the noise characteristics is represented by a ratio of the pixel energy Ve to the threshold value Th, i.e., Ve/Th, at a certain pixel position. A function that becomes closer to zero with decrease in the ratio and becomes closer to one with increase in the ratio is defined as the noise suppression level E. The noise suppression level E defined in Formula (4) may be used. FIG. 11 shows a graphic representation of Formula (4).

[Formula 4]

$$E = \frac{\exp(Th/Ve) - 1}{\exp(Th/Ve) + 1} \times 2 \times Ve/Th \quad (4)$$

(Noise Suppression Processing)

Then, the signals in each pixel of each of the band-limited image signals Bk are multiplied by the noise suppression levels E shown in Formula (5), obtained for each of the pixels of each of the band-limited image signals Bk as described above and the noise is suppressed. Consequently, the processed band-limited image signals fBk, of which noise has been suppressed, are obtained.

[Formula 5]

$$fBk = E \times Bk \quad (5)$$

(Generation of Processed Image Signal Sproc)

As described above, the noise suppression processing is performed on each of the band-limited image signals. After the processed band-limited image signals fBk are obtained, the processed image generating unit 4 subtracts the processed band-limited image signals fBk, of which noise component has been suppressed, from the band-limited image signals Bk, on which noise suppression processing has not been performed. Consequently, only noise components are extracted and band-limited noise image signals NBk are obtained for each of the band-limited image signals Bk. Specifically, signals representing noise components are obtained by subtracting the processed signals from the signals before processing for each of corresponding pixels using the images before noise suppression processing and the images after noise suppression processing. The band-limited noise image signals NBk are obtained by obtaining the signals representing the noise components for each of the band-limited images. Then, the noise image signal representing the noise components of the input image signal Sin is obtained by adding the band-limited noise image signals NBk together. The processed image signal Sproc, of which noise components has been suppressed, is obtained by subtracting the noise image signal from the input image signal Sin.

In the processed image generating unit 4, a subtractor 41 for obtaining the band-limited noise image signals by subtracting the processed band-limited image signals from the band-limited image signals; an interpolation processing means 42 for performing interpolation processing of the band-limited noise image signals; and an adder 43 for adding the band-limited noise image signals and the band-limited noise image signals, of which interpolation processing has been performed, are provided according to levels of the resolution level as illustrated in FIG. 5. Further, a second subtractor 44 is also provided. The second subtractor 44 obtains the processed image Sproc by subtracting the noise image signal, which has been obtained by repeating the addition by the adder 43, from the input image signal.

Figure 12:
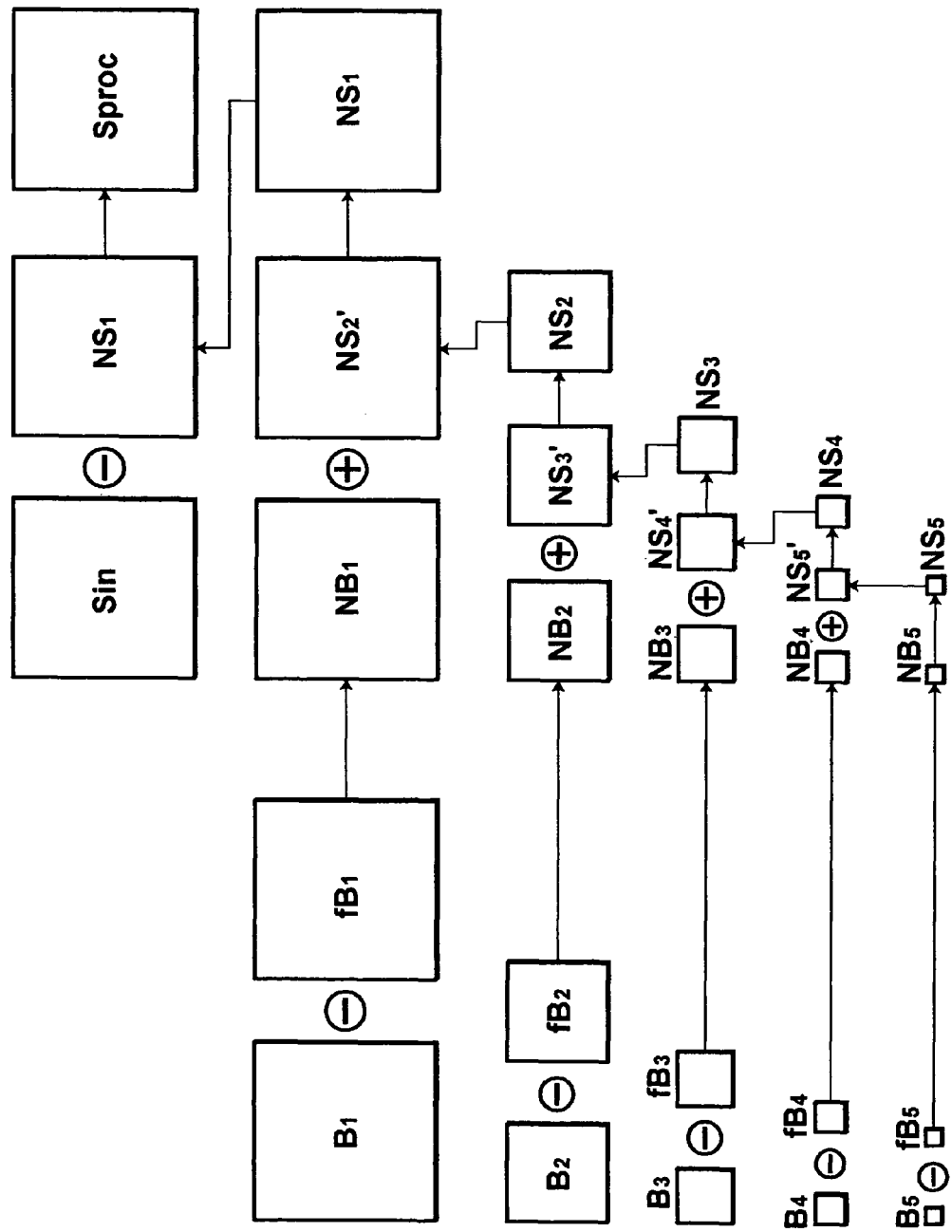
FIG. 12 shows a diagram schematically illustrating processing for generating processed images.

FIG. 12 schematically illustrates the processing for generating the processed image signal Sproc, of which noise components have been suppressed, based on the processed band-limited image signals fBk. When the processed band-limited image signals fBk (k=1 to n) are obtained, the band-limited noise image signals NBk are obtained by subtracting the processed band-limited image signals fBk from the band-limited image signals Bk by the subtractor 41 for each resolution level. Next, enlarged noise image signals NSn' are obtained by performing interpolation processing at the interpolation processing means 42 in the same manner as the interpolation processing means 11 so that a number of pixels of a lowest resolution signal NBn becomes the same as a number of pixels of a band-limited noise image signal NBk−1, of which the resolution is one-level higher, among the band-limited noise image signals Nbk. Then, the band-limited noise image signals NSn−1 are obtained by adding the band-limited noise image signals NBk−1 and the enlarged noise image signals NSn' together by the adder 43. The above-mentioned processing is repeated so that the resolution becomes higher and an addition noise image signal NS1, of which the resolution is the highest, is obtained. The addition noise image signal NS1, of which the resolution is the highest, is used as a noise image signal NSin corresponding to the input image signal Sin, which includes only noise components. Finally, the processed image signal Sproc is obtained by subtracting the noise image signal NSin from the input image signal Sin by the second subtractor.

In the step of repeatedly adding the band-limited noise image signals NBk−1 and the enlarged noise image signals NSn' together by the adder 43, an addition ratio between the band-limited noise image signals NBk−1 and the enlarged noise image signals NSn' may be controlled by multiplying the enlarged noise image signals NSn' by coefficients depending on the spatial frequencies and adding the result and the band-limited noise image signals NBk−1 together. Further, in the step of subtracting the noise image signal NSin from the input image signal Sin by the second subtractor, the noise suppression level may be further controlled by multiplying the noise image signal NSin by a coefficient depending on each signal value (density) of the input image signal Sin and subtracting the result from the input image signal Sin. It is empirically known that the lung field in a chest X-ray image has relatively high density and does not include much noise, for example. Since it is not very necessary to suppress the noise in the high density area, the signal values depending on the density may be adjusted in the case that the signal values indicating the noise components in noise images are corrected to be lower.

If an image is output based on the processed image signal Sproc, which has been obtained as described above, since the index value indicating the noise suppression level has been obtained based on the spatial frequencies in the radiographic image, as a kind of data correlated with the amount of noise components, as well as the X-ray dose during obtainment of the radiographic image and the noise suppression level has been controlled based on the index value, the noise can be suppressed more effectively.

An embodiment of the noise suppression processing apparatus according to the present invention has been described. However, the present invention is not limited to the embodiment as described above.

The band-limited image signals each having different frequency bands were obtained from the input image signal Sin by using the Laplacian pyramid technique in the above-mentioned embodiment. However, the band-limited image signals may be obtained by wavelet transformation as disclosed in Japanese Unexamined Patent Publication No. 6(1994)-274615, for example.

Further, the processed image signal is obtained by obtaining the noise image signal including only noise components and subtracting the noise image signal from the input image signal in the present embodiment. However, the processed image, in which noise components have been suppressed may be also obtained by directly carrying out inverse multi-resolution transformation (Laplacian pyramid reconstruction) on each of the band-limited image signals, of which noise components have been suppressed, as proposed in U.S. Patent Laid-Open No. 20020071600.

In the filter processing technique according to the present embodiment, the index value indicating the noise suppression level is obtained based on the index representing the X-ray dose and the index representing the spatial frequencies and the noise suppression level is controlled based on the index value. The filter processing technique may be also used in other filter processing. In the case that noise suppression processing (adaptive filter processing), which does not cause the edge to deteriorate more than required, is performed by obtaining reliability of the edge, as an index representing edge characteristics for each pixel of each of the band-limited image signals and applying an anisotropic filter (smoothing filter applied along the edge) and an isotropic filter (non-directional smoothing filter) by weighting as proposed in U.S. Laid-Open No. 20020071600, the filter processing technique may be adopted in the processing by the isotropic filter, for example.

Further, the pixel energy Ve is used to represent the local contrast of the signal in the present embodiment. However, any other value may be used as far as the local contrast can be represented. A variance value at a local area may be also used, for example.

Further, the noise suppression processing as described above may be executed by a computer. At this time, a program for causing the computer to execute the noise suppression processing may be distributed from a server. A computer-readable storage medium storing the program may be also provided.

What is claimed is:

1. A noise suppressing method for administering a noise suppression process on an input image signal representing a radiation image to suppress noise components included in the radiation image, comprising the steps of:
    generating a plurality of band limited image signals, each representing an image having different frequency bands, based on the radiation image;
    obtaining an index value indicating the level of noise suppression to be administered to suppress the noise components, based on data representing the radiation dose during obtainment of the radiation image, and data representing spatial frequencies of the radiation image;
    administering the noise suppression process on each of the plurality of band limited image signals based on the index value; and
    further comprising extracting the noise component for each of the plurality of band limited signals and subtracting the noise component for each of the plurality of band limited signals from an original radiation image.

2. A noise suppression processing method as defined in claim 1, wherein the step of obtaining the index value is a step for:
    calculating noise characteristics of the radiographic image based on the data representing the dose and the data representing the spatial frequencies;
    and deriving the index value based on the noise characteristics.

3. A noise suppression processing method as defined in claim 1, wherein the step of obtaining the index value is a step for:
    obtaining the index value for each pixel of band-limited images represented by the band-limited image signals.

4. A noise suppression processing method as defined in claim 3, wherein the step of obtaining the index value is a step for:
obtaining an evaluation value based on values of band-limited signals in the vicinity of the pixel;
and deriving the index value based on the evaluation value and the noise characteristics.

5. A noise suppression processing method as defined in claim 1, wherein the step of administering the noise suppression process is a step for:
performing the noise suppression processing on each of the pixels based on the index value of each of the pixels.

6. A noise suppression processing method as defined in claim 5, wherein the step of obtaining the index value is a step for:
obtaining an evaluation value based on values of band-limited signals in the vicinity of the pixel;
and deriving the index value based on the evaluation value and the noise characteristics.

7. A noise suppressing apparatus for administering a noise suppression process on an input image signal representing a radiation image to suppress noise components included in the radiation image, comprising:
a band limited image signal generating means for generating a plurality of band limited image signals, each representing an image having different frequency bands, based on the radiation image;
an index value obtaining means for obtaining an index value indicating the level of noise suppression to be administered to suppress the noise components, based on data representing the radiation dose during obtainment of the radiation image, and data representing spatial frequencies of the radiation image; and
a noise suppression processing means for administering the noise suppression process on each of the plurality of band limited image signals based on the index value; and
further comprising noise component extracting means for extracting the noise component for each of the plurality of band limited signals and subtracting the noise component for each of the plurality of band limited signals from an original radiation image.

8. A noise suppressing apparatus as defined in claim 7, wherein the index value obtaining means obtains the index value by:
calculating noise characteristics of the radiation image, based on the data representing the radiation dose and the data representing the spatial frequencies; and
deriving the index value based on the noise characteristics.

9. A noise suppressing apparatus as defined in claim 7, wherein:
the index value obtaining means obtains the index value for each pixel of the limited images represented by the band limited image signals; and
the noise suppression processing means administers the noise suppression process on each of the pixels, based on the index value for each of the pixels.

10. A noise suppressing apparatus as defined in claim 8, wherein:
the index value obtaining means obtains the index value for each pixel of the limited images represented by the band limited image signals, by calculating the noise characteristics thereof; and
the noise suppression processing means administers the noise suppression process on each of the pixels, based on the index value for each of the pixels.

11. A noise suppressing apparatus as defined in claim 10, wherein the index value obtaining means obtains the index values by:
obtaining evaluation values based on the band limited image signal in the vicinity of each of the pixels; and
deriving the index values based on the evaluation values and the noise characteristics.

12. A non-transitory computer-readable medium storing a program that causes a computer to execute a noise suppressing method for administering a noise suppression process on an input image signal representing a radiation image to suppress noise components included in the radiation image, comprising:
a procedure for generating a plurality of band limited image signals, each representing an image having different frequency bands, based on the radiation image;
a procedure for obtaining an index value indicating the level of noise suppression to be administered to suppress the noise components, based on data representing the radiation dose during obtainment of the radiation image, and data representing spatial frequencies of the radiation image;
a procedure for administering the noise suppression process on each of the plurality of band limited image signals based on the index value; and
further comprising a procedure for extracting the noise component for each of the plurality of band limited signals and subtracting the noise component for each of the plurality of band limited signals from an original radiation image.

13. A non-transitory computer-readable medium storing a program as defined in claim 12, wherein the procedure for obtaining the index value obtains the index value by:
calculating noise characteristics of the radiation image, based on the data representing the radiation dose and the data representing the spatial frequencies; and
deriving the index value based on the noise characteristics.

14. A non-transitory computer-readable medium storing a program as defined in claim 12, wherein:
the procedure for obtaining the index value obtains the index value for each pixel of the limited images represented by the band limited image signals; and
the procedure for administering the noise suppression process administers the noise suppression process on each of the pixels, based on the index value for each of the pixels.

15. A non-transitory computer-readable medium storing a program as defined in claim 13, wherein:
the procedure for obtaining the index value obtains the index value for each pixel of the limited images represented by the band limited image signals, by calculating the noise characteristics thereof; and
the process for administering the noise suppression process administers the noise suppression process on each of the pixels, based on the index value for each of the pixels.

16. A non-transitory computer-readable medium storing a program as defined in claim 15, wherein the procedure for obtaining the index value obtains the index value by:
obtaining evaluation values based on the band limited image signal in the vicinity of each of the pixels; and
deriving the index values based on the evaluation values and the noise characteristics.

* * * * *